United States Patent
Hellman et al.

(10) Patent No.: US 10,362,629 B2
(45) Date of Patent: *Jul. 23, 2019

(54) SYSTEMS AND METHODS FOR ESTABLISHING A COMMUNICATION LINK BETWEEN AN IMPLANTABLE MEDICAL DEVICE AND AN EXTERNAL INSTRUMENT

(71) Applicant: PACESETTER, INC., Sylmar, CA (US)

(72) Inventors: Heidi Hellman, Los Angeles, CA (US); Tejpal Singh, Stevenson Ranch, CA (US); Yongjian Wu, Saratoga, CA (US); Reza Shahandeh, Thousand Oaks, CA (US); Youjing Huang, San Jose, CA (US); Chao-Wen Young, Cupertino, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/004,228

(22) Filed: Jun. 8, 2018

(65) Prior Publication Data

US 2018/0295667 A1 Oct. 11, 2018

Related U.S. Application Data

(63) Continuation of application No. 15/851,556, filed on Dec. 21, 2017, now Pat. No. 10,021,733, which is a continuation of application No. 15/233,799, filed on Aug. 10, 2016, now Pat. No. 9,894,691.

(51) Int. Cl.
*H04W 4/80* (2018.01)
*H04W 76/28* (2018.01)
*H04W 76/10* (2018.01)
*A61B 5/07* (2006.01)

(52) U.S. Cl.
CPC ............. *H04W 76/28* (2018.02); *A61B 5/076* (2013.01); *H04W 4/80* (2018.02); *H04W 76/10* (2018.02); *H05K 999/99* (2013.01); *Y02D 70/00* (2018.01); *Y02D 70/10* (2018.01); *Y02D 70/14* (2018.01); *Y02D 70/144* (2018.01);

(Continued)

(58) Field of Classification Search
CPC .... H04B 1/0067; H04W 4/008; H04W 88/06; H04W 88/10
See application file for complete search history.

(56) References Cited

U.S. PATENT DOCUMENTS 9,288,614 B1* 3/2016 Young ................ A61N 1/37252
2004/0260363 A1* 12/2004 Von Arx ............ A61N 1/37252
607/60

(Continued)

*Primary Examiner* — David Bilodeau

(57) ABSTRACT

Systems and methods are provided for establishing a bi-directional communication link with an implantable medical device. The systems and methods include an implantable medical device (IMD) and an external instrument configured to establish a wireless bi-directional communication link there between over a wireless protocol. The wireless bi-directional communication link is established based on a scanning interval. The external instrument includes one or more processors electrically coupled to a radio frequency (RF) circuit and a memory device. The one or more processors are configured to define the scanning interval based on an advertising schedule received from the IMD.

20 Claims, 8 Drawing Sheets

(52) U.S. Cl.
CPC ............ *Y02D 70/162* (2018.01); *Y02D 70/20* (2018.01); *Y02D 70/26* (2018.01)

(56) References Cited

U.S. PATENT DOCUMENTS

| | | | | |
|---|---|---|---|---|
| 2006/0025834 A1* | 2/2006 | Von Arx | ................. | A61N 1/08 607/60 |
| 2011/0021142 A1* | 1/2011 | Desai | .................... | H04W 8/005 455/41.2 |
| 2014/0355582 A1* | 12/2014 | Kamath | ................ | H04W 84/20 370/338 |

* cited by examiner

SYSTEMS AND METHODS FOR ESTABLISHING A COMMUNICATION LINK BETWEEN AN IMPLANTABLE MEDICAL DEVICE AND AN EXTERNAL INSTRUMENT

CROSS REFERENCE TO RELATED APPLICATIONS

This application is a continuation of U.S. patent application Ser. No. 15/851,556, filed Dec. 21, 2017, now U.S. Pat. No. 10,021,733, which is a continuation of U.S. Pat. No. 9,894,691, filed Aug. 10, 2016.

BACKGROUND OF THE INVENTION

Embodiments of the present disclosure generally relate to systems and methods for establishing a bi-directional communication link between devices, and more particularly to establishing a communication link between implantable medical devices and external instruments based on an advertisement schedule.

An implantable medical device (IMD) is a medical device that is configured to be implanted within a patient anatomy and commonly employ one or more leads with electrodes that either receive or deliver voltage, current or other electromagnetic pulses from or to an organ or tissue for diagnostic or therapeutic purposes. In general, IMDs include a battery, electronic circuitry, such as a pulse generator and/or a microprocessor that is configured to handle RF communication with an external instrument as well as control patient therapy. The components of the IMD are hermetically sealed within a metal housing (generally referred to as the can).

IMDs are programmed by and transmit data to external instruments controlled by physicians and/or the patient. The external instruments use commercial operating systems (e.g., iOS, Android) that communicate by forming wireless bi-directional communication links with the IMDs. The bi-direction communication link is formed based on advertisement notices received by the external instruments broadcasted by the IMD at a predetermined frequency. The predetermined frequency is based on the wireless protocol. However, the current drain expended by the IMD to broadcast the advertisement notices can be too high where small size is of utmost importance. To conserve current drain, the advertising notices may be output at a lower frequency than defined by the wireless protocol. That is, the period between advertisement notices may be on the order of minutes instead of seconds or milliseconds.

However, the external instruments have built in constraints related to how long the external instrument will monitor for advertising notices for usability and power consumption purposes. If the advertisement notice is not received by the external instrument within the monitoring period the external instrument may repeatedly monitor for advertising notices during the monitoring period at decreasing intervals until the advertisement notice is received. Due to the lower frequency of the advertising notices transmitted by the IMD, if the external instrument misses an advertising pulse, minutes may pass by before the external instrument has an opportunity to receive an advertisement notice during the monitoring period. The number of unsuccessful monitoring periods occurring between advertisement notices drain the power source, such as the battery, of the external instrument. A need exists for improved methods and systems to establish a communication link between the external instrument and an IMD having a modified advertisement notice broadcast frequency.

BRIEF SUMMARY

In accordance with an embodiment herein, a method is provided for establishing a bi-directional communication link. The method includes configuring an external instrument to define a scanning interval based on an advertising schedule transmitted by a medical device implanted in a patient. The method further includes configuring the external instrument to establish a wireless bi-directional communication link with the implantable medical device (IMD) based on an advertisement notice occurring during the scanning interval defined by a wireless protocol. The method further includes delivering therapy to the patient in accordance with therapeutic protocols stored in the IMD or communicated to the IMD by the external instrument.

In an embodiment, a system for establishing a bi-directional communication link is provided. The system includes an implantable medical device (IMD) having a sensing circuit to collect sensed data. The IMD includes a radio frequency (RF) circuit and a memory. The memory includes an advertising schedule based on a wireless protocol. The IMD is configured to transmit the advertising schedule during a first communication session to an external instrument. The external instrument includes one or more processors that are electrically coupled to an RF circuit and a memory. The one or more processors are configured to define a scanning interval based on the advertising schedule. The RF circuit of the external instrument is configured to establish a wireless bi-directional communication link with the IMD over the wireless protocol based on the scanning interval.

DETAILED DESCRIPTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Various embodiments described herein include a method and/or system to provide an advertising notice schedule to establish a wireless bi-directional communication link between an implantable medical device (IMD) and an external instrument (EI). The advertising schedule is based on a modified advertisement interval relative to a wireless protocol defining the wireless bi-directional communication link. For example, the advertising schedule may include information on when subsequent advertising notices are to be transmitted by the IMD, an advertisement interval or frequency of transmissions of the advertising notices by the IMD, and/or the like. The EI defines a scanning interval to monitor for advertisement notices delivered by the IMD. The scanning interval is configured by the EI based on the advertising schedule such that the scanning interval occurs concurrently with and/or is synchronous with the advertisement notice. For example, the EI will delay the scanning interval to listen for the advertising notice until the EI knows the advertising notice is scheduled to be output from the IMD. The EI calculates when the advertising notice is scheduled to be transmitted by the IMD based on information included in the advertising schedule such as an advertising interval, an advertising delay, and/or the like. When the EI and IMD establish the wireless bi-directional communication link, the IMD may transmit the advertising schedule to the EI, prior to termination of the link, in order to adjust the timing information between the IMD and the EI for subsequent communication sessions.

A technical effect of various embodiment described herein allow an adjusted (e.g., slower) advertising rate without an impact to the time it takes to establish a wireless bi-directional communication link between the IMD and the EI. A technical effect of various embodiments described herein include decreasing battery drain for both the IMD and the EI to establish a wireless bi-directional communication link.

Figure 1:
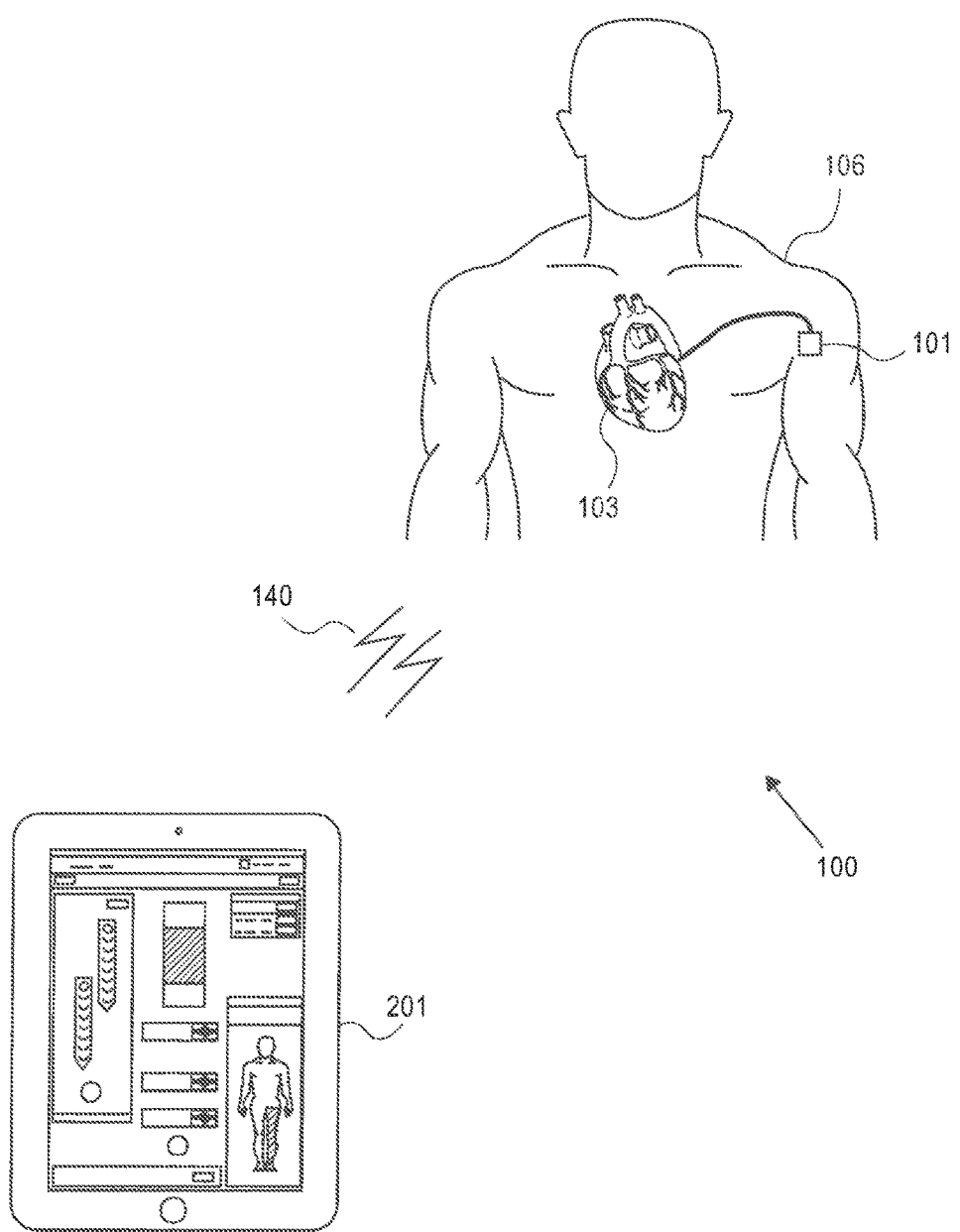
FIG. 1 illustrates simplified block diagram of a system for initiating a bi-directional communication link, according to an embodiment of the present disclosure.

FIG. 1 illustrates a simplified block diagram of a system 100 for initiating a bi-directional communication link. The system 100 may include an IMD 101 and an EI 201 (e.g., tablet computer, smart phone, smart watch, laptop, and/or the like), according to an embodiment. The IMD 101 may be implanted within a patient 106 (e.g., proximate to and/or within a heart 103, proximate to the spinal cord). Additionally or alternatively, the IMD 101 may have components that are external to the patient, for example, the IMD 101 may include a neuro external pulse generator (EPG). Optionally, the IMD 101 may be one of various types of implantable devices, such as, for example, neurostimulator, electrophysiology (EP) mapping and radio frequency (RF) ablation system, an implantable pacemaker, implantable cardioverter-defibrillator (ICD), defibrillator, cardiac rhythm management (CRM) device, an implantable pulse generator (IPG), or the like.

Optionally, the IMD 101 may be a leadless pacer, examples of which are disclosed in U.S. Pat. No. 9,072,913, entitled, "RATE RESPONSIVE LEADLESS CARDIAC PACEMAKER," and U.S. Pat. No. 9,168,383, entitled "LEADLESS CARDIAC PACEMAKER WITH CONDUCTED COMMUNICATION," METHOD OF FABRICATING STIMULATION LEAD FOR APPLYING ELECTRICAL STIMULATION TO TISSUE OF A PATIENT," which are expressly incorporated herein by reference. Additionally or alternatively, the IMD 101 may be a leadless monitor, example of which are disclosed in U.S. Pat. No. 9,949,660, filed Mar. 29, 2016, entitled, "METHOD AND SYSTEM TO DISCRIMINATE RHYTHM PATTERNS IN CARDIAC ACTIVITY," which is expressly incorporated herein by reference.

The EI 201 is configured to establish a wireless bi-directional communication link 104 with the IMD 101. The communication link 104 allows the EI 201 to receive measurements from the IMD 101, and to program or send instructions to the IMD 101. The communication link 104 may use a standard wireless protocol such as Bluetooth Low Energy, Bluetooth, Medical Implant Communication Service, and/or the like. The EI 201 may be located within a home of the patient 106, a hospital, an automobile, at an office of the patient 106, or the like.

Figure 2:
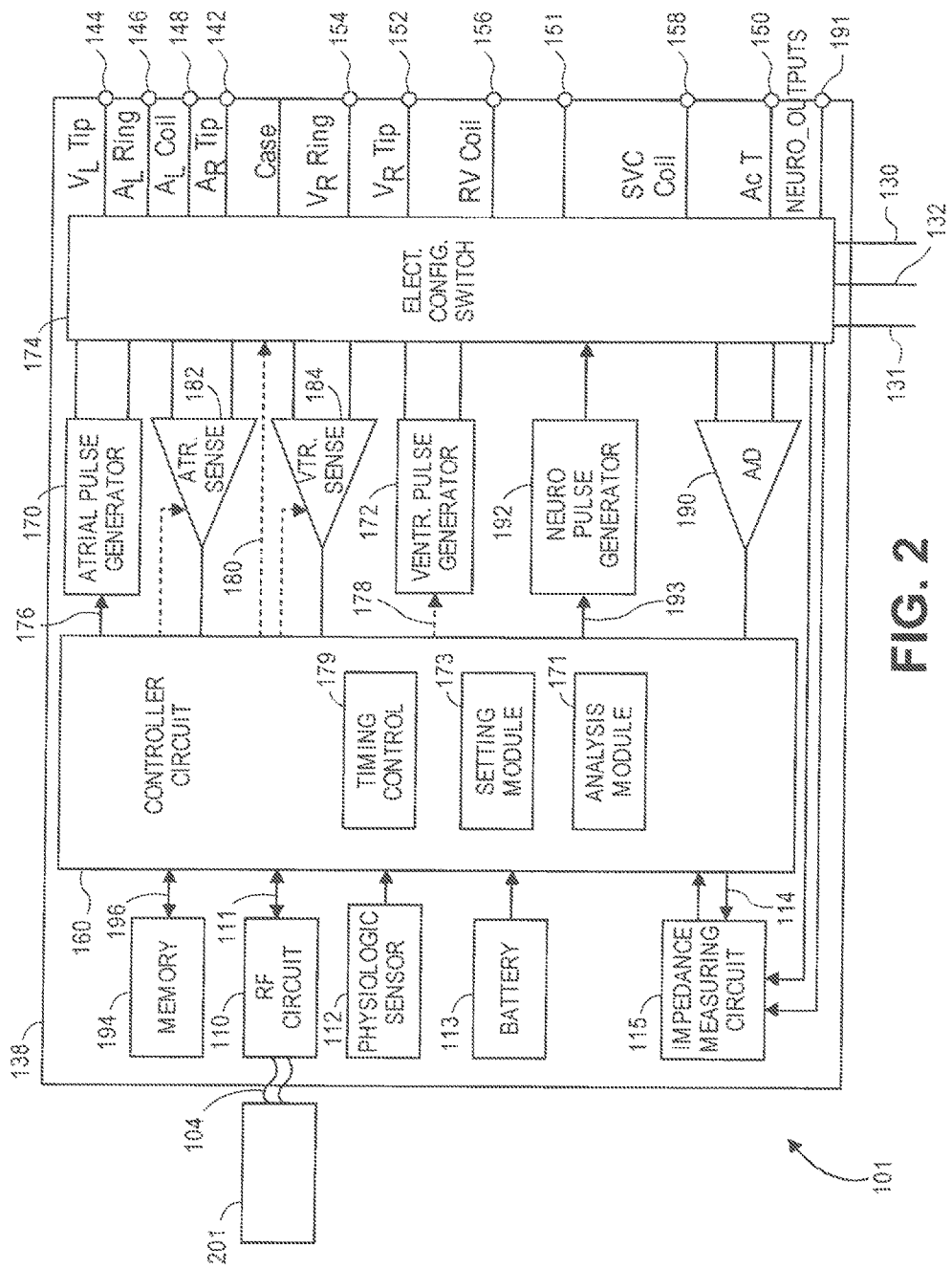
FIG. 2 illustrates a block diagram of exemplary internal components of an implantable medical device, according to an embodiment of the present disclosure.

FIG. 2 illustrates a block diagram of exemplary internal components of the IMD 101. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, one or more of these devices may be hard-wired with logic circuits to perform these operations.

The IMD 101 is for illustration purposes only, and it is understood that the circuitry could be duplicated, eliminated or disabled in any desired combination to provide a device capable of treating the appropriate chamber(s) with cardioversion, defibrillation and/or pacing stimulation as well as providing for apnea detection and therapy. Additionally or alternatively, the IMD 101 may be used to generate electrical stimulation for application to a desired area of a body, such as a spinal cord stimulation, as described later herein corresponding to FIG. 8.

The housing 138 for the IMD 101, shown schematically in FIG. 2, is often referred to as the "can", "case" or "case electrode" and may be programmably selected to act as the return electrode for all "unipolar" modes. The housing 138 may further be used as a return electrode alone or in combination with one or more of the coil electrodes for shocking purposes. The housing 138 further includes a connector (not shown) having a plurality of terminals, 142, 152, 154, 156 and 158 (shown schematically and, for convenience, the names of the electrodes to which they are connected are shown next to the terminals. A right atrial tip terminal ($A_R$ TIP) 142 is adapted for connection to the atrial tip electrode and a right atrial ring terminal may be adapted for connection to right atrial ring electrode. A left ventricular tip terminal ($V_L$ TIP) 144, a left atrial ring terminal ($A_L$ RING) 146, and a left atrial shocking terminal ($A_L$ COIL) 148 are adapted for connection to the left ventricular ring electrode, and a left atrial tip electrode and a left atrial coil electrode respectively. A right ventricular tip terminal ($V_R$ TIP) 152, a right ventricular ring terminal ($V_R$ RING) 154, a right ventricular shocking terminal ($R_V$ COIL) 156, and an SVC shocking terminal (SVC COIL) 158 are adapted for connection to the right ventricular tip electrode, right ventricular ring electrode, an RV coil electrode, and an SVC coil electrode, respectively.

An acoustic terminal (ACT) 150 is adapted to be connected to an external acoustic sensor or an internal acoustic sensor, depending upon which (if any) acoustic sensors are used. Terminal 151 is adapted to be connected to a blood sensor to collect measurements associated with glucose levels, natriuretic peptide levels, or catecholamine levels.

The IMD 101 includes a controller circuit 160 which controls operation of the IMD 101. The controller circuit 160 (also referred to herein as a processor module or unit) may include one or more processors, or equivalent control circuitry, designed specifically for controlling the delivery of stimulation therapy and may further include RAM or ROM memory, logic and timing circuitry, state machine circuitry, and I/O circuitry. Typically, the controller circuit 160 includes the ability to process or monitor input signals (data) as controlled by program code stored in memory. The details of the design and operation of the controller circuit 160 are not critical to the invention. Rather, any suitable controller circuit 160 may be used that carries out the functions described herein. Among other things, the controller circuit 160 receives, processes, and manages storage of digitized cardiac data sets from the various sensors and electrodes. For example, the cardiac data sets may include IEGM data, pressure data, heart sound data, and the like.

The IMD 101 includes an atrial pulse generator 170 and a ventricular/impedance pulse generator 172 to generate pacing stimulation pulses for delivery by the right atrial lead 130, the right ventricular lead 131, and/or the coronary sinus lead 132 via an electrode configuration switch 174. It is understood that in order to provide stimulation therapy in each of the four chambers of the heart, the atrial and ventricular pulse generators, 170 and 172, may include dedicated, independent pulse generators, multiplexed pulse generators or shared pulse generators. The pulse generators, 170 and 172, are controlled by the controller circuit 160 via appropriate control signals, 176 and 178, respectively, to trigger or inhibit the stimulation pulses.

The IMD 101 includes a neuro stimulation pulse generator circuit 192 to generate stimulation pulses for a brain or spinal cord nervous system. The stimulation pulses are delivered by a plurality of electrodes through the neuro output lead 191. The neuro stimulation pulse generator circuit 192 is controlled by the controller circuit 160 via appropriate control signals 193 to trigger or generate the stimulation pulses.

The controller circuit 160 further includes timing control circuitry 179 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the controller circuit 160, determines the polarity of the stimulation pulses (e.g., unipolar, bipolar, etc.) by selectively closing the appropriate combination of switches (not shown) as is known in the art.

Atrial sensing circuit 182 and ventricular sensing circuit 184 may also be selectively coupled to the right atrial lead 130, coronary sinus lead 132, and the right ventricular lead 131, through the switch 174 for collecting sensed data corresponding cardiac activity in each of the four chambers of the heart. Accordingly, the atrial (ATR SENSE) and ventricular (VTR SENSE) sensing circuits, 182 and 184, may include dedicated sense amplifiers, multiplexed amplifiers or shared amplifiers. The outputs of the atrial and ventricular sensing circuits, 182 and 184, are connected to the controller circuit 160 which, in turn, receives the sensed data and is able to trigger or inhibit the atrial and ventricular pulse generators, 170 and 172, respectively, in a demand fashion in response to the absence or presence of cardiac activity in the appropriate chambers of the heart.

Cardiac signals are also applied to the inputs of an analog-to-digital (A/D) data acquisition system 190. The data acquisition system 190 is configured to acquire IEGM signals, convert the raw analog data into a digital IEGM signal, and store the digital IEGM signals in memory 194 for later processing and/or RF transmission to the EI 201. The data acquisition system 190 is coupled to the right atrial lead 130, the coronary sinus lead 132, and the right ventricular lead 131 through the switch 174 to sample cardiac signals across any combination of desired electrodes. The data acquisition system 190 may also be coupled, through switch 174, to one or more of the acoustic sensors. The data acquisition system 190 acquires, performs A/D conversion, produces and saves the digital pressure data, and/or acoustic data.

The controller circuit 160 controls the acoustic sensor and/or a physiologic sensor to collect heart sounds during one or more cardiac cycles. The heart sounds include sounds representative of a degree of blood flow turbulence. The acoustic sensor and/or physiologic sensor collects the heart sounds that include S1, S2 and linking segments. The controller circuit 160 may change a value for at least one of the pacing parameters between the cardiac cycles. The controller circuit 160 implements one or more processes described herein to determine values for one or more pacing parameters that yield a desired level of hemodynamic performance.

The controller circuit 160 includes an analysis module 171 and a setting module 173 that function in accordance with embodiments described herein. The analysis module 171 analyzes a characteristic of interest from the heart sounds within at least a portion of the linking segment. The setting module 173 sets a desired value for the pacing parameter based on the characteristic of interest from the heart sounds for at least the portion of the linking segment. The pacing parameter may represent at least one of an AV delay, a VV delay, a VA delay, intra-ventricular delays, electrode configurations and the like. The controller circuit 160 changes at least one of the AV delay, the VV delay, the VA delay, the intra-ventricular delays, electrode configurations and like in order to reduce systolic turbulence and regurgitation.

The RF circuit 110 may be configured to handle and/or manage the bi-directional communication link between the IMD 101 and the EI 201. The RF circuit 110 is controlled by the controller circuit 160 and may support one or more wireless communication protocols while communicating with the EI 201, such as Bluetooth low energy, Bluetooth, Medical Implant Communication Service (MICS), and/or the like. The RF circuit 110 may include a transmitter, receiver, and/or a transceiver. Optionally, the RF circuit 110 may be electrically coupled to an antenna (not shown), such as the antenna described in U.S. patent application Ser. No. 15/154,758, filed May 13, 2016, entitled, "IMPLANTABLE DEVICE HEADER WITH EMBEDDED SENSOR AND ANTENNA," which is expressly incorporated herein by reference. Protocol firmware may be stored in memory 194, which is accessed by the controller circuit 160. The protocol firmware provides the wireless protocol syntax for the controller circuit 160 to assemble data packets, establish communication links 104, and/or partition data received from the EI 201.

The controller circuit 160 is coupled to the memory 194 by a suitable data/address bus 196, wherein the programmable operating parameters used by the controller circuit 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, Sv02 data and the like for a desired period of time (e.g., 1 hour, 24 hours, 1 month). The memory 194 may store instructions to direct the controller circuit 160 to analyze the cardiac signals and heart sounds identify characteristics of interest and derive values for predetermined statistical parameters.

The pacing and other operating parameters of the IMD 101 may be non-invasively programmed into the memory 194 through the RF circuit 110 in bi-directional wireless communication with the EI 201. The RF circuit 110 is controlled by the controller circuit 160 and receives data for transmission by a control signal 111. The RF circuit 110 allows intra-cardiac electrograms, pressure data, acoustic data, Sv02 data, and status information relating to the operation of IMD 101 (as contained in the controller circuit 160 or memory 194) to be sent to the EI 201 through an established bi-directional communication link 104. The RF circuit 110 also allows the EI 201 to program new pacing parameters for the setting module 173 used by the IMD 101.

To establish the communication link 104 between the EI 201 and the IMD 101, the controller circuit 160 may instruct the RF circuit 110 to transmit an advertisement notice on an advertisement channel corresponding to the select communication initialization mode of the wireless protocol. The advertisement channel is a point to multipoint, unidirectional, channel to carry a repeating pattern of system information messages such as network identification, allowable RF channels to establish the communication link 104, and/or the like that is included within the advertisement notice. The advertisement notice may be repeatedly transmitted after a set duration or an advertisement interval based on an advertising schedule stored in the memory 194 until the communication link 104 is established with the EI 201.

The IMD 101 may also include a physiologic sensor 112, such as an accelerometer commonly referred to as a "rate-responsive" sensor because it is typically used to record the activity level of the patient or adjust pacing stimulation rate according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 138 of the IMD 101.

Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. The IMD 101 is shown as having impedance measuring circuit 115 which is enabled by the controller circuit 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be obtained.

Figure 3:
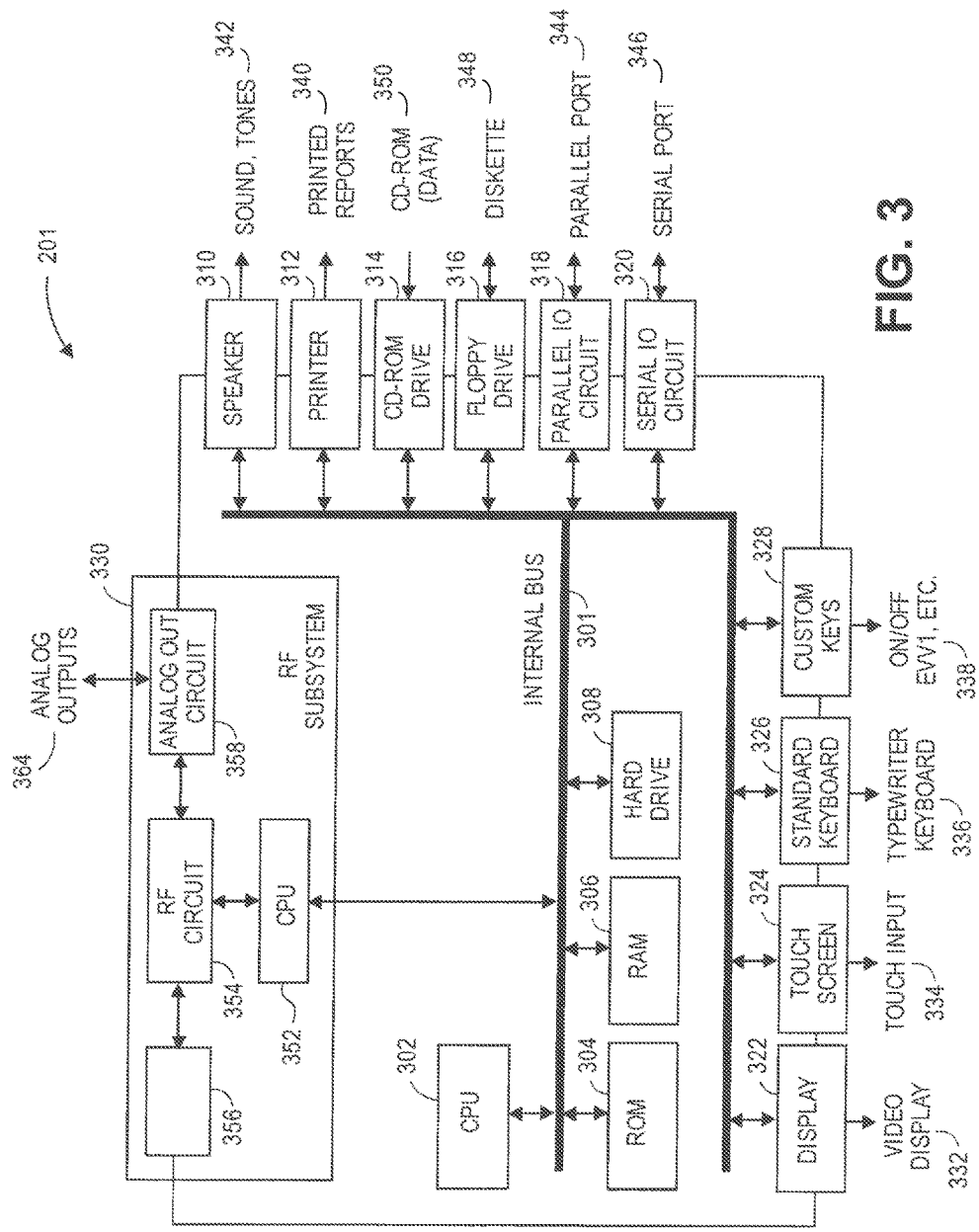
FIG. 3 illustrates a block diagram of exemplary internal components of an external instrument, according to an embodiment of the present disclosure.

FIG. 3 illustrates a functional block diagram of the EI 201 that is operated in accordance with the processes described herein and to interface with the IMD 101 as described herein. The EI 201 may be a workstation, a portable computer, a tablet computer, a smart watch, an IMD programmer, a PDA, a cell phone and/or the like. The EI 201 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, the display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a micro-controller, or equivalent control circuitry, designed specifically to control interfacing with the EI 201 and with the IMD 101. The CPU 302 may include RAM or ROM memory, logic and timing circuitry, state machine circuitry, and I/O circuitry to interface with the IMD 101. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the EI 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the EI 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350.

The RF subsystem 330 includes a central processing unit (CPU) 352 in electrical communication with an RF circuit 354, which may communicate with both memory 356 and an analog out circuit 358. The analog out circuit 358 includes communication circuits to communicate with analog outputs 364. The EI 201 may wirelessly communicate with the IMD 101 and utilize protocols, such as Bluetooth, Bluetooth low energy, MICS, and/or the like. For example, the memory 356, ROM 304, and/or RAM 306 may include Protocol firmware, which is accessed by the CPU 352 and/or 302. The protocol firmware provides the wireless protocol syntax for the CPU 352 and/or 302 160 to assemble data packets, establish communication links 104, and/or partition data received from the IMD 101.

Figure 4:
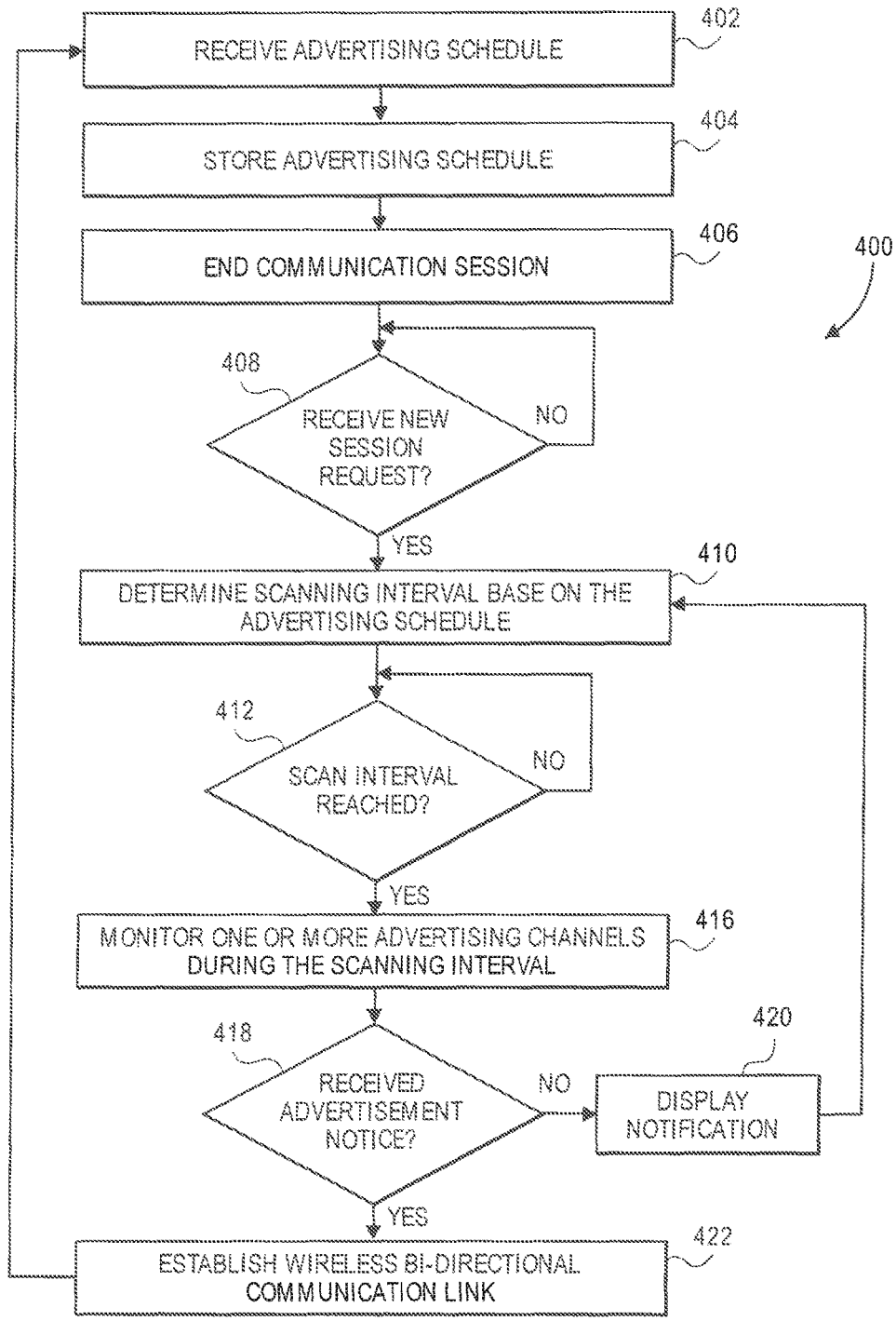
FIG. 4 illustrates a flowchart of a method for establishing a bi-directional communication link with an implantable medical device.

FIG. 4 illustrates a flowchart of a method 400 for establishing a bi-directional communication link between the EI 201 and the IMD 101. The method 400 may be implemented as a software algorithm, package, or system that directs one or more hardware circuits or circuitry to perform the actions described herein. For example, the operations of the method 400 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the circuit or circuit firmware.

FIG. 4 will be described in reference to FIGS. 5A-B.

Figure 5A:
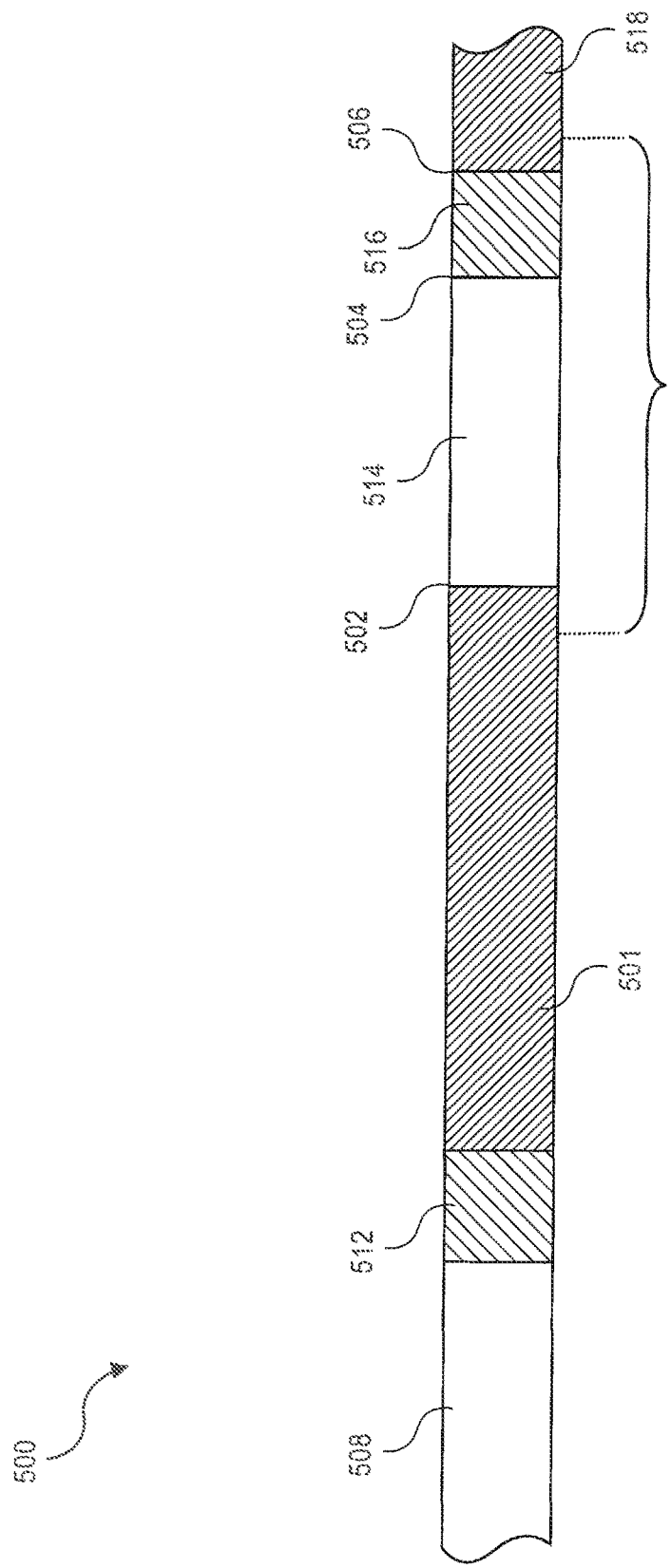
FIG. 5A illustrates a timing diagram of establishing wireless bi-directional communication links between an implantable medical device and an external instrument, according to an embodiment of the present disclosure.

FIG. 5A is a timing diagram 500 of establishing the wireless bi-directional communication link 104 between the IMD 101 and the EI 201. The timing diagram 500 includes two communication sessions, a first communication session 501 and a second communication session 518. During the communication sessions 501, 518 the IMD 101 and the EI 201 may exchange data packets along the wireless bi-directional communication link 104. Each of the communication sessions 501, 518 are established by the IMD 101 and the EI 201 based on an advertisement state 508, 514 and an establishing state 512, 516 defined by the wireless protocol of the wireless bi-directional communication link 104.

During the advertising state 508 and 514, the IMD 101 may periodically transmit data packets corresponding to advertisement notices along one or more advertising channels. For example, the advertisement notice may be repeated, at a set interval corresponding to an advertisement interval. The advertisement notices may include frequency synchronization information utilized to form the communication link 104, address information of the IMD 101, address information of the EI 201, pairing and/or bonding information, and/or the like to form the wireless bi-directional communication link 104. The information contained in the advertisement notice may be utilized by the EI 201 to establish the wireless bi-directional communication link 104 during the establishing state 512 and 516.

The establishing state 512 and 516 may correspond to the EI 201 receiving the advertisement notice and transmitting a request to the IMD 101 to establish the wireless bi-directional communication link 104. During the establishing state 512 and 516, the EI 201 may monitor the one or more advertisement channels during a scanning interval for the advertisement notice. The scanning interval corresponds to a length of time the EI 201 may listen to the one or more advertising channels to receive the advertisement notice. When the EI 201 receives the advertisement notice, the EI 201 may transmit a data packet representing a connection request along the advertisement channel of the received advertisement notice to the IMD 101. The connection request may include instructions, such as a frequency of the data channel for the wireless bi-directional communication link 104. When the IMD 101 receives and confirms the connection request, the IMD 101 may monitor the data channel identified within the connection request for further instructions from the EI 201, thereby establishing the bi-directional communication link 104 starting the communication sessions 501, 518. Additionally or alternatively, the EI 201 and the IMD 101 may initiate a pairing and/or bonding procedure as described in U.S. patent application Ser. No. 14/091,809, entitled, "SYSTEM AND METHODS FOR ESTABLISHING A COMMUNICATION SESSION BETWEEN AN IMPLANTABLE MEDICAL DEVICE AND AN EXTERNAL DEVICE," which is expressly incorporated herein by reference.

During the communication sessions 501 and 518, the IMD 101 may transmit sensed data of the patient. For example, the IMD 101 may transmit cardiac information, patient physiological information, pulsing information, and/or the like acquired by the IMD 101. The EI 201 may receive the sensed data from the IMD 101. Additionally or alternatively, the EI 201 may reconfigure the IMD 101. For example, the EI 201 may transmit new stimulation parameters, clear the sensed data store in the memory 194, and/or the like. The EI 201 and/or the IMD 101 may further terminate the communication sessions 501 and 518 closing the wireless bi-directional communication link 104 between the EI 201 and the IMD 101. When the link 104 is closed, the IMD 101 may begin transmitting the advertising notices returning to the advertising state 512 and 514.

In connection with FIG. 4, the IMD 101 adjusts and/or updates the EI 201 to an advertising schedule utilized by the IMD 101 during the advertisement states 508, 514. Based on the advertising schedule, the EI 201 may adjust and/or configure the scanning interval during the establishing state 512 and 516 based on the advertising schedule. The advertising schedule may include information on one or more parameters of the IMD 101 during the advertisement state 508, 514.

Beginning at 402 (FIG. 4), the EI 201 may receive the advertising schedule from the IMD 101. In reference to FIG. 5B, the IMD 101 may include the advertising schedule within a data packet 530a during the first communication session 501.

Figure 5B:
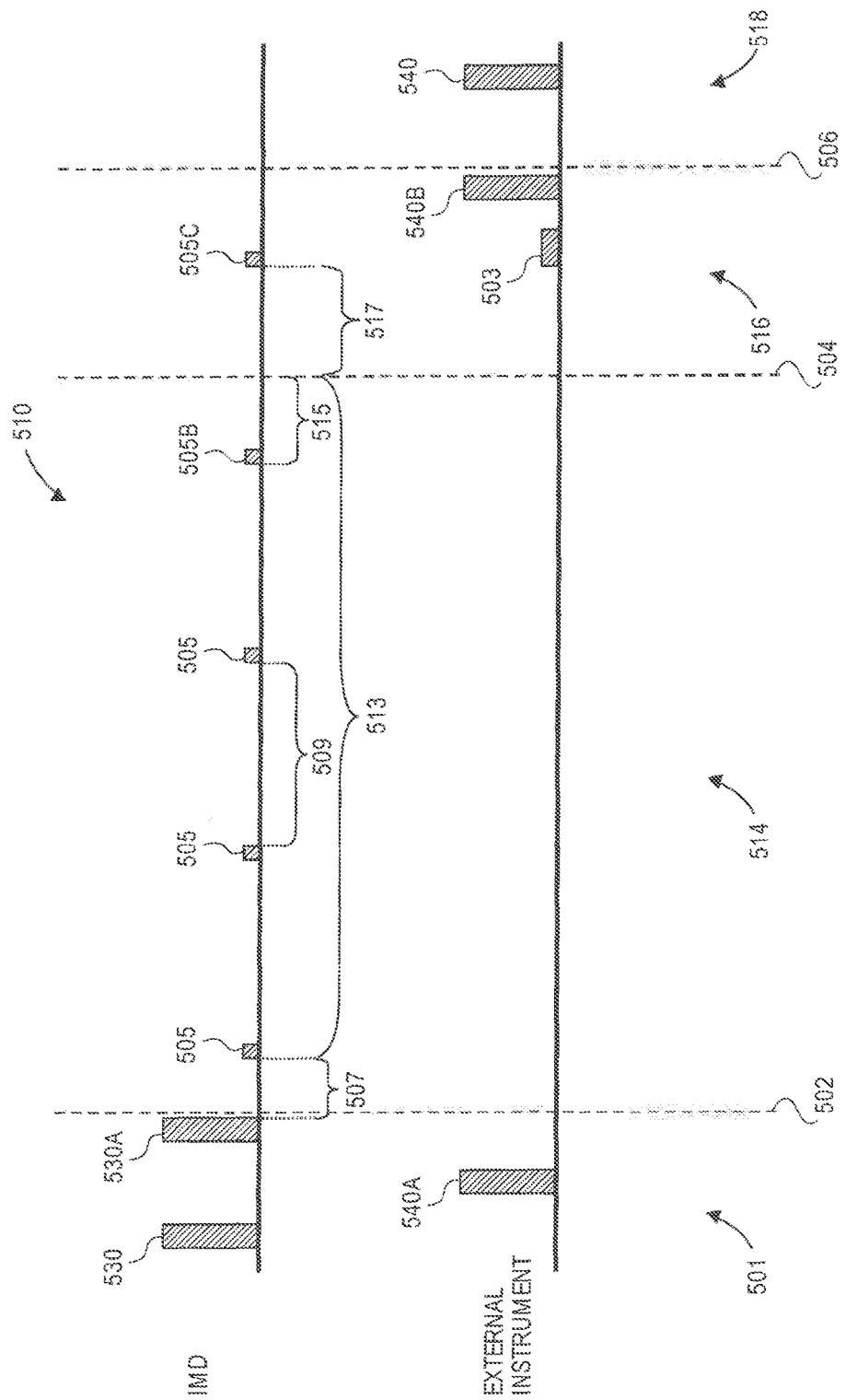
FIG. 5B illustrates a timing diagram of transmissions between an implantable medical device and an external instrument during a segment of the timing diagram of FIG. 5A, according to an embodiment of the present disclosure.

FIG. 5B illustrates a timing diagram of transmissions between the IMD 101 and the EI 201 during a segment 510 of the timing diagram 500 of FIG. 5A. The segment 510 illustrates signals and/or data transmitted between the IMD 101 and the EI 201 during a portion of the first and second communication session 501 and 518, the advertisement state 514, and the establishing state 516. For example, during the communication sessions 501 and 518 the IMD 101 and the EI 201 may exchange data as data packets 530 (including 530a) and 540 (including 540 a-b), respectively. In various embodiments, the data packets 530 transmitted by the IMD 101 may include cardiac information, patient physiological information, pulsing information, and/or the like acquired by the IMD 101.

Additionally or alternatively, the advertising schedule may be included within one or more of the data packets 530, such as the data packet 530a. The advertising schedule within the data packet 530a may include information on when subsequent advertising notices are to be transmitted by the IMD 101. For example, the advertising schedule may include an advertisement delay 507 that corresponds to a length of time for the transmission of a first advertising notice 505a subsequent to a termination (e.g., at 502) of the first communication session 501. The advertisement delay 507 may be a number of clock ticks (e.g., based on an internal system clock of the IMD 101), a timestamp, and/or the like. Optionally, the advertising schedule may include an advertisement interval 509 corresponding to a length of time between transmission of consecutive advertisement notices (e.g., 505*b* and 505*c*). Additionally or alternatively, the advertising schedule may include a frequency of transmissions of the advertising notices 505, and/or the like. It may be noted that the advertisement interval 509 of the advertising schedule conflicts with the wireless protocol of the wireless bi-directional communication link 104. For example, the advertisement interval 509 utilized by the IMD 101 during the advertisement state 514 may contradict and/or fall outside the specified length of the advertisement interval 509 provided in the wireless protocol for the wireless bi-directional communication link 104.

For example, the EI 201 and the IMD 101 may utilize the Bluetooth Low Energy ("BLE") protocol. The BLE protocol is defined within "Bluetooth Specification Version 4.1," published Dec. 3, 2013 (incorporated herein by reference). The BLE protocol defines an advertisement interval to have a length less than or equal to ten milliseconds. In various embodiments, the advertising schedule followed by the IMD 101 defines the advertisement interval 509 that is greater than ten milliseconds (e.g., more than two minutes). By having an advertisement interval 509 greater than ten milliseconds, the advertisement interval 509 is not within the defined length of the advertising schedule as provided by the BLE protocol and conflicts with the BLE protocol.

The IMD 101 may transmit the advertising schedule within the data packet 530*a* in response to an advertising schedule request and/or termination request from the EI 201. For example, a termination request for the first communication session 501 may be included in the data packet 540*a* from the EI 201. The IMD 101 may receive the data packet 540*a* via the RF circuit 111. The controller circuit 160 may verify the termination request by comparing particular frames of the data packet 540*a* (e.g., a header of the data packet, the payload of the data packet, and/or the like). When the controller circuit 160 verifies the termination request of the data packet 540*a*, the controller circuit 160 instructs the RF circuit 111 to transmit the data packet 530*a* that includes the advertising schedule to the EI 201. Optionally, the data packet 530*a* may include a confirmation that the termination request has been received by the IMD 101.

At 404 (FIG. 4), the EI 201 may store the advertising schedule. For example, in reference to FIG. 5B, the EI 201 may receive the data packet 530*a* via the RF subsystem 330. The CPU 352 or 302 may partition the advertising schedule from the data packet 530*a* based on the protocol syntax and store the advertising schedule in the memory 356, ROM 304, RAM 306, and/or the hard drive 308.

At 406 (FIG. 4), the EI 201 and the IMD 101 may end the communication session. For example, in reference to FIG. 5B, when the controller circuit 160 verifies the termination request of the data packet 540*a*, the controller circuit 160 may terminate or close the bi-directional communication link 104 referenced as 502. In another example, the EI 201 may terminate or close the bi-directional communication link when the data packet 530*a* containing the advertising schedule is received.

After the bi-directional communication link 104 is terminated (referenced as 502 in FIGS. 5A-B) the IMD 101 may continually broadcast the one or more advertisement notices 505 (including 505*a-c*) over one or more advertisement channels based on the advertising schedule and the advertisement interval 509. For example, the timing diagram 510 illustrates a series of advertisement notices 505 transmitted by the IMD 101 along one or more advertisement channels. The advertisement notices 505 represent a data packet that may contain frequency synchronization information utilized to form the bi-directional communication link 104, address information of the IMD 101, address information of the EI 201, and/or the like as defined by the wireless protocol. Additionally or alternatively, the advertisement notice 505 may include pairing and/or bondable information (e.g., passkey seed information). The advertisement notice 505 is repeated based on the advertisement interval 509, until the wireless bi-directional communication link 104 is established. The advertisement interval 509 represents a length of time between advertisement notices 505 transmitted by the IMD 101. The advertisement interval 509 may be predetermined and stored in the memory 194.

At 408 (FIG. 4), the CPU 302 may determine when a request 504 for a new communication session is received. The request 504 may correspond to a received instruction by the EI 201 and/or the RF subsystem 330 to establish a wireless bi-directional communication link 104 with the IMD 101. The request 504 may be received based on a predetermined schedule stored in the ROM 304, RAM 306, and/or hard drive 308. For example, the predetermined schedule may correspond to a plurality of connection times on when to acquire information (e.g., cardiac information, patient physiological information, pulsing information, and/or the like) from the IMD 101. During one of the connection times, the CPU 302 may determine a request 504 for a new communication is received, and to instruct the RF subsystem 330 to establish a wireless bi-directional communication link 104 with the IMD 101. Additionally or alternatively, the request 504 may be received in response to a user input from the touchscreen 324 and/or standard keyboard 336. For example, the user operating the EI 201 may select a graphical icon of a graphical user interface shown on the display 322 that represents a connection request. Based on the received selection of the graphical icon, the CPU 302 may determine that the request 504 to form a wireless bi-directional communication link 104 with the IMD 101 is received.

At 410, the CPU 302 may determine a scanning interval 503 based on the advertising schedule. During the scanning interval 503, the EI 201 monitors the one or more advertisement channels to detect one or more of the advertisement notices 505. For example, the CPU 302 (FIG. 3) of the EI 201 instructs the RF subsystem 330 to monitor one or more advertisement channels during the scanning interval 503. A length of the scanning interval 503 may be a predetermined length store in the memory 356, the ROM 304, the RAM 306, and/or hard drive 308. Optionally, the scanning interval 503 may be configured by the user, such that, the scanning interval 503 may be increased or decreased based on a user input received by the touchscreen 324 or standard keyboard 326. The CPU 302 may determine when the scanning interval 503 is to occur relative to the request 504 based on the advertising schedule. For example, the CPU 302 may configure the timing on when the scanning interval 503 occurs to be synchronous with and/or occurs during (e.g., concurrent with) the transmission of a subsequent advertisement notice 505*c* with respect to the request 504. The CPU 302 may configure when the scanning interval 503 occurs to increase the probability of the scanning interval 503 occurring during at least one of the advertisement notices 505 transmitted by the IMD 101 relative to scanning intervals that are aligned with the requirements wireless protocol. A technical effect of the scanning interval 503 configured by the CPU 302 may reduce a number of needed scanning intervals 503 of the EI 201 in order to form a bi-directional communication link 104 with the IMD 101. As described in connection FIG. 6, the CPU 302 may determine when the advertisement notice 505c occurs based on the advertising schedule received within the data packet 530a.

Figure 6:
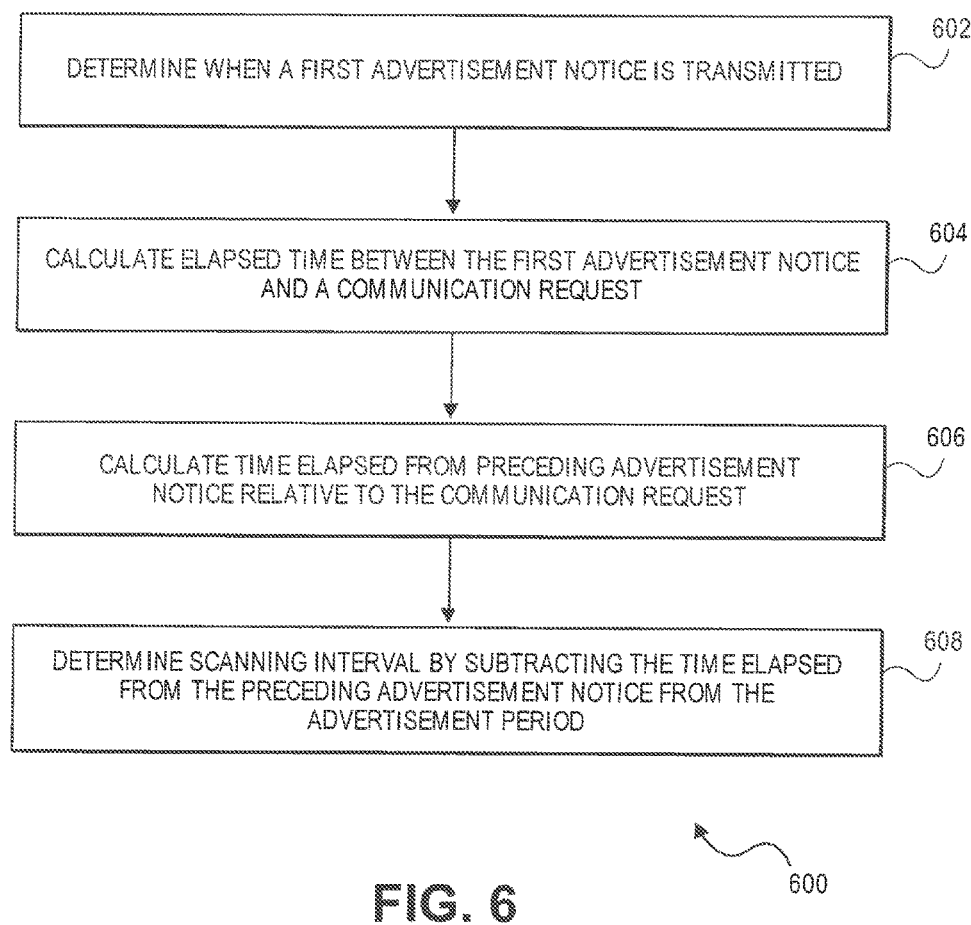
FIG. 6 illustrates a flowchart of a method to calculate a scanning interval based on an advertising schedule, according to an embodiment of the present disclosure.

FIG. 6 illustrates a flowchart of a method 600 to calculate a time of the scanning interval 503 based on the advertising schedule, according to an embodiment of the present disclosure. The method 600 may be implemented as a software algorithm, package, or system that directs one or more hardware circuits or circuitry to perform the actions described herein. For example, the operations of the method 400 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the circuit or circuit firmware.

Beginning at 602, the CPU 302 may determine when the first advertisement notice 505a is transmitted by the IMD 101. For example, in connection with FIGS. 4 and 5B, at 402, the CPU 302 may receive the advertising schedule from the IMD 101 based on the data packet 530a. The advertising schedule includes the advertisement delay 507 between the data packet 530a to the first advertisement notice 505a. For example, the advertisement delay 507 may be a number of clock ticks corresponding to an amount of time in seconds, such as 120 seconds. Additionally or alternatively, the CPU 302 may retrieve the advertising schedule stored in the memory 356, the ROM 304, the RAM 306, and/or hard drive 308 (e.g., at 404 of FIG. 4). Based on the advertising schedule, the EI 201 may calculate when the first advertising notice 505a will be transmitted by the IMD 101 subsequent to the termination of the communication session 501. For example, the CPU 302 may add the advertisement delay 507 to a timestamp of the data packet 530a. The timestamp may correspond to when the EI 201, such as the RF subsystem 330, receives the data packet 530a. Additionally or alternatively, the timestamp may correspond to when the data packet 530a was transmitted by the IMD 101. For example, the EI 201 may identify the timestamp based on a header of the data packet 530a. The EI 201 may store the calculated time of the first advertising notice 505a in the memory 356, the ROM 304, the RAM 306, and/or the hard drive 308.

At 604, the CPU 302 may calculate an elapsed time 513 between the first advertisement notice 505a and the communication request (e.g., the request 504). For example, the request 504 is received at a receive timestamp. The CPU 302 may determine the elapsed time 513 between the first advertisement notice 505a and the request 504 by subtracting the calculated time determined at 602 from the receive timestamp.

At 606, the CPU 302 may calculate an elapsed time 515 from a preceding advertisement notice 505 (e.g., the advertising notice 505b) relative to the communication request (e.g., the request 504). For example, the CPU 302 may perform a modulo operation to identify a remainder after division of the elapsed time 513 by the advertisement interval 509. The remainder representing the elapsed time 515.

At 608, the CPU 302 may determine the scanning interval 503 by subtracting the elapsed time 515 from the advertisement interval 509. For example, by subtracting the elapsed time 515 from the advertisement interval 509 the CPU 302 determines a time delay 517 from the request 504 to when the subsequent advertisement notice 505c is likely to occur. Based on the time delay 517, the CPU 302 may determine when the scanning interval 503 occurs. For example, the CPU 302 may instruct the RF subsystem 330 to monitor the one or more advertisement channels after the time delay 517 during a time period corresponding to the scanning interval 503.

Additionally or alternatively, the CPU 302 may reduce the time delay 517 by a predetermined tolerance. The predetermined tolerance may be stored in the ROM 304, RAM 306, and/or hard drive 308. The predetermined tolerance may be configured to adjust the scanning interval 503 to occur prior to the calculated time of the advertisement notice 505c by the CPU 302. For example, based on the predetermined tolerance the CPU 302 may configure the scanning interval 503 to precede the advertisement notice 505c to increase a likelihood the advertisement notice 505c transmitted by the IMD 101 occurs during and/or subsequent to a start of the scanning interval 503.

Additionally or alternatively, the above method 600 may form Equation 1. The variable G represents when the scanning interval 503 occurs, and the variable D represents the advertisement interval 509. The variable C represents the receive time stamp of when the request 504 is received by the CPU 302. The variable B represents the elapsed time 515.

$$G = D - ((C-B) \bmod D) \quad \text{Equation 1}$$

Returning to FIG. 4, at 412, the CPU 302 may determine if the scanning interval 503 is reached. For example, when the request 504 is received the CPU 302 may delay the scanning interval 503 until the time delay 517 (e.g., calculated at 608) after the request 504 is reached. In another example, the CPU 302 may delay the scanning interval 503 until the time delay 517 with the predetermined tolerance is reached.

At 416, the CPU 302 may instruct the RF subsystem 330 to monitor one or more of the advertisement channels based on the advertising schedule corresponding to the scanning interval 503.

At 418, the CPU 302 may determine if the advertisement notice 505c is received. For example, the EI 201 receives the advertisement notice 505c, in the form of a data packet transmitted from the IMD 101, the CPU 302 analyzes or compares the data packet with the protocol syntax stored in the memory 356, the ROM 304, the RAM 306, or the hard drive 308. The protocol syntax may include the structure of the advertisement notice 505 (e.g., data packet specifications, appropriate number of bits, frequency, or the like) utilized by the wireless protocol. Optionally, the advertisement notice 505c may include a unique code designating the packet as an advertisement notice. By comparing the protocol syntax with the data packet, the CPU 302 determines whether the received data packet is the advertisement notice 505c using the wireless protocol of the EI 201. If the received data packet is determined not to be an advertisement notice, the EI 201 may determine the advertisement notice 505c was not received.

If the advertisement notice 505c was not received, then at 420, the CPU 302 may instruct the display 322 to display a notification. For example, the notification may correspond to a connection error indicative that the request 504 for the wireless bi-directional communication link 104 failed. Additionally or alternatively, the CPU 302 may automatically calculate a subsequent scanning interval based on the advertising interval 509. For example, the CPU 302 may instruct the RF subsystem 330 to monitor one or more of the advertisement channels corresponding to the subsequent scanning interval after the advertising interval 509. Optionally, the CPU 302 may adjust a length of the subsequent scanning interval. For example, the subsequent scanning interval may have a longer length relative to the scanning interval 503. Additionally or alternatively, the CPU 302 may adjust the predetermined tolerance to determine the scanning interval At 422, the EI 201 and the IMD 101 may establish the wireless bi-directional communication link 104. When the CPU 302 determines that the data packet received by the RF subsystem 330 is the advertisement notice 505c (e.g., having the proper syntax), the CPU 302 outputs a connection request, such as within a payload of the data packet 540b to be transmitted by the RF subsystem 330 along the advertisement channel. The CPU 302 constructs the data packet 540b representing the connection request by adding packet frames and/or a payload corresponding to the one or more communication link parameters such as the address of the IMD 101 and/or EI 201, error detection codes such as CRC, the communication interval (e.g., length of time between data packets 530, 540), a data channel map, and/or the like. Additionally or alternatively, the payload may include connection instructions (e.g., frequency of the data channel for the wireless bi-directional communication link 104) for the IMD 101. When the data packet 340b has been formed, the CPU 302 outputs the data packet to the RF subsystem 330 to be transmitted along the advertisement channel corresponding to the advertisement channel of the advertisement notice 505c transmitted from the IMD 101.

The data channel map may correspond to a subset of data channels of the RF channels defined by the wireless protocol. The data channels of the data channel map correspond to the one or more frequencies that can be used by the EI 201 and the IMD 101 for the wireless bi-directional communication link 104. The data channels selected for the data channel map may be based on a previous bi-directional communication link 104 (e.g., the first communication session 501) between the EI 201 and the IMD 101, data channels that are used by the EI 201 for alternative wireless bi-directional communication links with other devices (e.g., based on an advertising schedule), and/or the like.

The RF circuit 110 of the IMD 101 receives the data packet 540b corresponding to the connection request. The RF circuit 110 may demodulate the RF signal and output the data packet 540b to the controller circuit 160 via the interconnect 111. The controller circuit 160 may store the data packet in the memory 194 for analysis. The controller circuit 160 determines whether the data packet 540b is in response to the advertisement notice 505c by comparing the address information of the data packet 540b with the address information transmitted by the IMD 101 within the advertisement notice 505c. If the address information matches, the controller circuit 160 partitions the payload from the data packet 540b and carries out the instruction of the connection request from the payload by comparing the instructions to a stored instruction set store in the memory 194 for the wireless protocol. Optionally, the controller circuit 160 may compare the address information of the EI 201 within the data packet 540b with a permissible links table stored in the memory 194 to determine whether the connection request should be ignored by the IMD 101 or partition the payload of the data packet 540b.

When the controller circuit 160 identifies the connection request, the controller circuit 160 may instruct the RF circuit 110 to monitor the select data channel identified in the one or more communication link parameters for further instructions from the EI 201, thereby establishing the bi-directional communication link 104 at 506.

Additional examples of forming a communication link between an IMD and an EI (e.g., external device) is disclosed in U.S. patent application Ser. No. 14/091,809, entitled, "SYSTEM AND METHODS FOR ESTABLISHING A COMMUNICATION SESSION BETWEEN AN IMPLANTABLE MEDICAL DEVICE AND AN EXTERNAL INSTRUMENT," which is expressly incorporated herein by reference.

Figure 7:
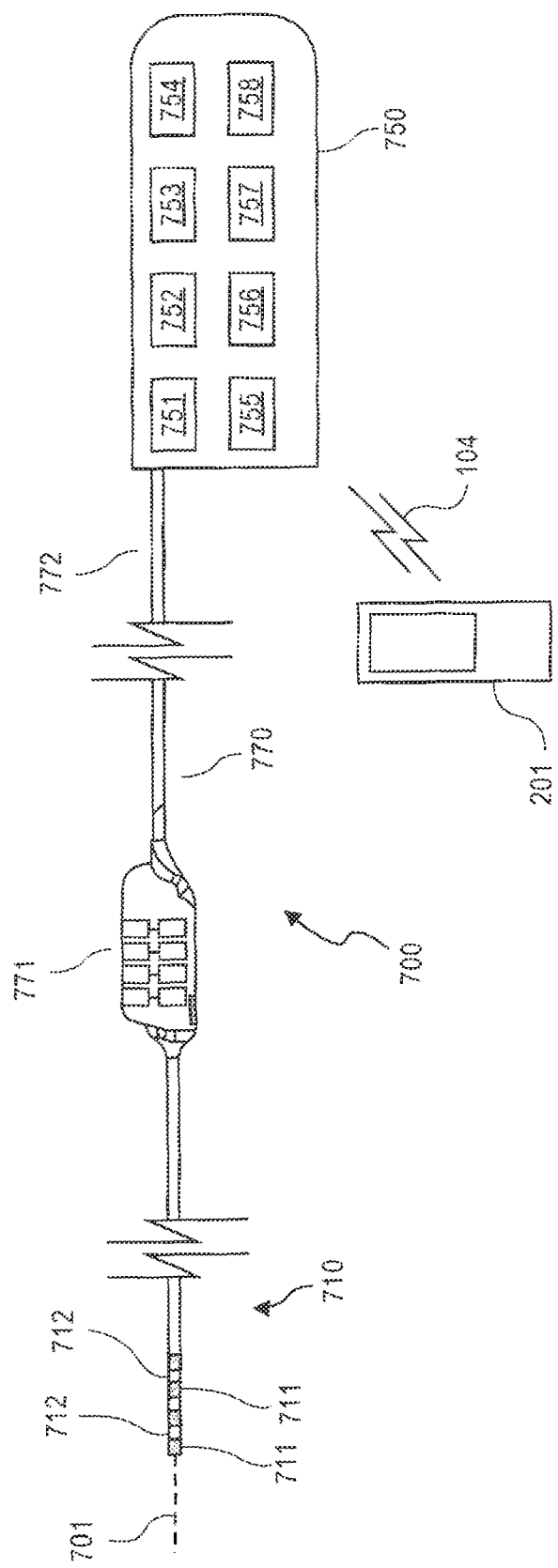
FIG. 7 illustrates a block diagram of exemplary internal components of an implantable medical device, according to an embodiment of the present disclosure.

FIG. 7 illustrates a block diagram of exemplary internal components of an IMD 700, in accordance with an embodiment. For example, the IMD 700 may be a neurostimulator adapted to stimulate spinal cord tissue, peripheral nerve tissue, deep brain tissue, cortical tissue, cardiac tissue, digestive tissue, pelvic floor tissue, or any other suitable nerve tissue of interest within a patient's body.

The IMD 700 may include an implantable pulse generator (IPG) 750 that is adapted to generate electrical pulses applied to the tissue of a patient. Additionally or alternatively, the IPG 750 may be an external neuro pulse generator. The IPG 750 typically comprises a metallic housing that encloses a controller 751, pulse generating circuitry 752, a charging coil 753, a battery 754, RF circuit 755, battery charging circuitry 756, switching circuitry 757, memory 758, and the like.

The controller 751 (also referred to herein as a processor module or unit) typically includes a microprocessor, or equivalent control circuitry, designed specifically for controlling the components of the IPG 750 and may further include RAM or ROM memory, logic and timing circuitry, state machine circuitry, and I/O circuitry. Typically, the controller 751 includes the ability to process or monitor input signals (data) as controlled by program code stored in memory. The details of the design and operation of the controller 751 are not critical to the invention. Rather, any suitable controller 751 may be used that carries out the functions described herein.

The IPG 750 may comprise a separate or an attached extension component 770. If the extension component 770 is a separate component, the extension component 770 may connect with a "header" portion of the IPG 750 as is known in the art. If the extension component 770 is integrated with the IPG 750, internal electrical connections may be made through respective conductive components. Within the IPG 750, electrical pulses are generated by the pulse generating circuitry 752 and are provided to the switching circuitry 757. The switching circuitry 757 connects to outputs of the IPG 750. Electrical connectors (e.g., "Bal-Seal" connectors) within the connector portion 771 of the extension component 770 or within the IPG header may be employed to conduct various stimulation pulses. The terminals of one or more leads 710 are inserted within connector portion 771 or within the IPG header for electrical connection with respective connectors. Thereby, the pulses originating from the IPG 750 are provided to the leads 710. The pulses are then conducted through the conductors of the lead 710 and applied to tissue of a patient via stimulation electrodes 711 that may be coupled to blocking capacitors. Any suitable known or later developed design may be employed for connector portion 771.

The stimulation electrodes 711 may be positioned along a horizontal axis 702 of the lead 710, and are angularly positioned about the horizontal axis 702 so the stimulation electrodes 711 do not overlap. The stimulation electrodes 711 may be in the shape of a ring such that each stimulation electrode 711 continuously covers the circumference of the exterior surface of the lead 710. Each of the stimulation electrodes 711 are separated by non-conducting rings 712, which electrically isolate each stimulation electrode 711 from an adjacent stimulation electrode 711. The non-conducting rings 712 may include one or more insulative materials and/or biocompatible materials to allow the lead 710 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 711 may be configured to emit the pulses in an outward radial direction proximate to or within a stimulation target. Additionally or alternatively, the stimulation electrodes 711 may be in the shape of a split or non-continuous ring such that the pulse may be directed in an outward radial direction adjacent to the stimulation electrodes 711. Examples of a fabrication process of the stimulation electrodes 711 is disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is expressly incorporated herein by reference.

It should be noted the stimulation electrodes 711 may be in various other formations, for example, in a planar formation on a paddle structure as disclosed in U.S. Provisional Application No. 61/791,288, entitled, "PADDLE LEADS FOR NEUROSTIMULATION AND METHOD OF DELIVERING THE SAME," which is expressly incorporated herein by reference.

The lead 710 may comprise a lead body 772 of insulative material about a plurality of conductors within the material that extend from a proximal end of lead 710, proximate to the IPG 750, to its distal end. The conductors electrically couple a plurality of the stimulation electrodes 711 to a plurality of terminals (not shown) of the lead 710. The terminals are adapted to receive electrical pulses and the stimulation electrodes 711 are adapted to apply the pulses to the stimulation target of the patient. Also, sensing of physiological signals may occur through the stimulation electrodes 711, the conductors, and the terminals. It should be noted that although the lead 710 is depicted with four stimulation electrodes 711, the lead 710 may include any suitable number of stimulation electrodes 711 (e.g., less than four, more than four) as well as terminals, and internal conductors. Additionally or alternatively, various sensors (e.g., a position detector, a radiopaque fiducial) may be located near the distal end of the lead 710 and electrically coupled to terminals through conductors within the lead body 772.

For implementation of the components within the IPG 750, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 756) of an IPG 750 using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 752) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 750. Different pulses on different stimulation electrodes 711 may be generated using a single set of the pulse generating circuitry 752 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads 711 as is also known in the art. Various sets of parameters may define the pulse characteristics and pulse timing for the pulses applied to the various stimulation electrodes 711 as is known in the art. Although constant current pulse generating circuitry is contemplated for some embodiments, any other suitable type of pulse generating circuitry may be employed such as constant voltage pulse generating circuitry.

The stimulation parameters (e.g., amplitude, frequency, type of stimulation waveform) and other operating parameters of the IMD 700 may be non-invasively programmed into the memory 758 through the RF circuit 755 in bi-directional wireless communication link 104. For example, the external device 201 may permit the user to move electrical stimulation along and/or across one or more of the lead(s) 710 using different stimulation electrode 711 combinations by communicating to the IMD 700, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. The controller 751 controls the RF circuit 755 and receives data/transmissions from the RF circuit 755. The RF circuit 755 further allows status information relating to the operation of IMD 700 (as contained in the controller 751 or memory 758) to be sent to via the bi-directional communication link 104.

The controller 751 may support a particular wireless communication protocol while communicating with the external device 201, such as Bluetooth low energy, Bluetooth, ZigBee, Medical Implant Communication Service ("MICS"), or the like. Protocol firmware may be stored in memory 758, which is accessed by the controller 751. The protocol firmware provides the wireless protocol syntax for the controller 751 to assemble data packets, establish communication links 104, and partition data received from the bi-directional communication link 104.

The memory 758 may also contain a pre-defined algorithm that generates a passkey. The passkey may be used to initiate a bonding procedure between the IMD 700 and the external device 201 to establish a secured bi-directional communication session over the bi-directional communication link 104. The passkey may be generated based on a dynamic seed and/or a static identification received by the RF circuit 755 through the bi-directional communication link 104 from the external device 201 and inputted into the pre-defined algorithm. Optionally, the dynamic seed may be a random number generated by the controller 751, based on the local system clock of the IMD 700, or the like that is transmitted by the RF circuit 755 to the external device. Additionally or alternatively, the static identification may be stored on the memory 758 representing a product serial identification number of the IMD 700, which is a unique number assigned to the IMD 700 by a manufacturer of the IMD 700. Optionally, the static identification may be a pre-determined number stored on the memory 758 set by a user.

The controller 751, the microcontroller 160, and CPUs 302 and 352 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controller 751, the microcontroller 160, and CPUs 302 and 352 represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 751, the microcontroller 160, and CPUs 302 and 352 may execute a set of instructions that are stored in one or more storage elements, in order to process data. The storage elements may also store data or other information as desired or needed. The storage element may be in the form of an information source or a physical memory element within the controller 751, the microcontroller 160, and CPUs 302 and 352. The set of instructions may include various commands that instruct the controller 751, the microcontroller 160, and CPUs 302 and 352 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(t), unless and until such claim limitations expressly use the phrase "means for" followed by a statement of function void of further structure.

What is claimed is:

1. A system for establishing a bi-directional communication link comprising:
an implantable medical device (IMD) configured to operate in accordance with a wireless protocol, the IMD having a sensing circuit to collect sensed data, a first radio frequency (RF) circuit and a memory configured to store an advertising schedule based on the wireless protocol, wherein the advertising schedule includes an advertisement interval having a length longer than a defined advertisement interval of the wireless protocol; and
an external instrument configured to operate in accordance with a wireless protocol, the external instrument having one or more processors electrically coupled to a second RF circuit and a memory, the IMD configured to transmit the advertising schedule to the external instrument during a first communication session with the external instrument, the one or more processors of the external instrument being configured to define a scanning interval for the external instrument based on the advertising schedule transmitted to the external instrument from the IMD, the RF circuit of the external instrument is configured to establish a wireless bi-directional communication link with the IMD over the wireless protocol based on the scanning interval.

2. The system of claim 1, wherein the memory is further configured to store the wireless protocol syntax in the IMD memory.

3. The system of claim 1, wherein the RF circuit of the IMD is further configured to periodically transmit an advertisement notice along a dedicated advertisement channel based on the advertising schedule.

4. The system of claim 3, wherein the advertising schedule includes an advertisement delay defining a length of time a first advertisement notice is transmitted relative to a termination of the first communication session.

5. The system of claim 1, wherein the RF circuit of the IMD is configured to transmit first and second advertisement notices based on the advertising schedule, the one or more processors are configured to receive a request for a communication session interposed between the first and second advertisement notices.

6. The system of claim 5, wherein the request is based on a user input or a predetermined schedule stored in the memory.

7. The system of claim 5, wherein the external instrument is configured scan during the second advertisement notice.

8. The system of claim 5, wherein the scanning interval is based on when the request is received.

9. The system of claim 1, wherein the advertising schedule is transmitted by the IMD in response to a termination request transmitted by the external instrument.

10. The system of claim 1, wherein the wireless protocol constitutes at least one of a Bluetooth protocol, a Bluetooth low energy protocol, or a Medical Implant Communication Service protocol.

11. A method for establishing a bi-directional communication link between an implantable medical device (IMD) and an external instrument, the method comprising:
   determining an advertising schedule having an advertising interval with a length longer than a defined advertisement interval of an wireless protocol;
   storing the advertising schedule in the IMD;
   configuring the IMD to periodically transmit an advertisement notice through a dedicated advertisement channel based on the advertisement interval of the advertising schedule;
   transmitting the advertising schedule from the IMD to the external instrument;
   configuring the external instrument to define a scanning interval based on the advertising schedule transmitted by the implantable medical device (IMD); and
   configuring the external instrument to establish a wireless bi-directional communication link with the IMD.

12. The method of claim 11, further comprising storing the wireless protocol syntax in the IMD memory.

13. The method of claim 11 wherein the advertising schedule includes an advertisement delay defining a length of time until the advertisement notice is transmitted by the IMD subsequent to a termination of a first communication session.

14. The method of claim 11, further comprising receiving a request for a communication session at the external instrument interposed between a preceding advertisement notice and the advertisement notice.

15. The method of claim 14, wherein the receiving operation is based on a user input or a predetermined schedule.

16. The method of claim 14, wherein the scanning interval is defined based on when the request is received.

17. The method of claim 14, wherein the scanning interval is defined based on a length of time between the preceding advertisement notice and when the request is received.

18. The method of claim 11, wherein the scanning interval is defined to occur during the advertisement notice.

19. The method of claim 11, further comprising configuring the IMD to transmit the advertising schedule in response to a termination request transmitted by the external instrument.

20. The method of claim 11, wherein the wireless protocol constitutes at least one of a Bluetooth protocol, a Bluetooth low energy protocol, or a Medical Implant Communication Service protocol.

* * * * *